US007270802B2

(12) United States Patent
Loghman-Adham

(10) Patent No.: US 7,270,802 B2
(45) Date of Patent: Sep. 18, 2007

(54) NON-LETHAL TEMPORARY INCAPACITATION FORMULATION AND NOVEL SOLVENT SYSTEM

(75) Inventor: Kamran Loghman-Adham, Gaithersburg, MD (US)

(73) Assignee: Zarc International, Inc., Minonk, IL (US)

( * ) Notice: Subject to any disclaimer, the term of this patent is extended or adjusted under 35 U.S.C. 154(b) by 885 days.

(21) Appl. No.: 10/036,546

(22) Filed: Jan. 7, 2002

(65) Prior Publication Data

US 2003/0129138 A1 Jul. 10, 2003

(51) Int. Cl.
*A61K 9/12* (2006.01)
*A01N 25/02* (2006.01)

(52) U.S. Cl. .......................................... 424/45; 424/43

(58) Field of Classification Search ................ 424/439, 424/401, 45, DIG. 1, 47, 43; 514/844
See application file for complete search history.

(56) References Cited

U.S. PATENT DOCUMENTS

| | | | | |
|---|---|---|---|---|
| 4,097,607 | A | 6/1978 | Larson | |
| 4,192,892 | A | 3/1980 | Thorsell | |
| 4,316,917 | A * | 2/1982 | Antoshkiw et al. | 426/540 |
| 4,739,990 | A | 4/1988 | Aguirre | |
| 4,869,897 | A * | 9/1989 | Chatterjee et al. | 424/47 |
| 4,883,659 | A * | 11/1989 | Goodman et al. | 424/78.03 |
| 5,059,437 | A * | 10/1991 | Todd, Jr. | 426/250 |
| 5,217,708 | A | 6/1993 | Pinkney | |
| 5,273,748 | A | 12/1993 | Walker | |
| 5,286,475 | A * | 2/1994 | Louvet et al. | 424/45 |
| 5,307,960 | A | 5/1994 | Fay | |
| 5,429,301 | A | 7/1995 | Franks | |
| 5,464,624 | A | 11/1995 | Isbell | |
| 5,476,192 | A | 12/1995 | Julinot | |
| 5,500,205 | A | 3/1996 | Abbott | |
| 5,655,461 | A | 8/1997 | Gilbert | |
| 5,698,180 | A | 12/1997 | Dixon | |
| 5,698,191 | A | 12/1997 | Wiersma | |
| 5,796,330 | A | 8/1998 | Vinette | |
| 5,804,203 | A * | 9/1998 | Hahn et al. | 424/401 |
| 5,821,450 | A | 10/1998 | Fedida | |
| 5,942,212 | A * | 8/1999 | Lentini et al. | 424/59 |
| 6,135,321 | A | 10/2000 | Hippensteel | |
| 6,159,474 | A | 12/2000 | Davidson | |
| 6,348,200 | B1 * | 2/2002 | Nakajima et al. | 424/401 |
| 2001/0016215 | A1 | 8/2001 | Pinkney | |
| 2001/0032413 | A1 | 10/2001 | Neumann | |
| 2001/0034964 | A1 | 11/2001 | Neumann | |
| 2002/0058053 | A1 * | 5/2002 | Nakanishi et al. | 424/401 |
| 2002/0192273 | A1 * | 12/2002 | Buseman et al. | 424/449 |
| 2003/0134780 | A1 * | 7/2003 | Patt | 514/6 |
| 2004/0167046 | A1 * | 8/2004 | Lukenbach et al. | 510/135 |

FOREIGN PATENT DOCUMENTS

| | | | |
|---|---|---|---|
| JP | 56089832 | * | 7/1981 |
| JP | 2000204046 | * | 7/2000 |

* cited by examiner

*Primary Examiner*—Alton Pryor
(74) *Attorney, Agent, or Firm*—Berenato, White & Stavish, LLC

(57) ABSTRACT

A non-lethal temporarily incapacitating formulation having a new solvent system that has reduced blow back longer hang time when used as an aerosol spray. The solvent and formulation are non-toxic, non-hazardous, non-flammable, highly stable, environmentally safe and able to withstand extreme operating temperatures. The solvent system is a mixture of propylene glycerol dicaprylate/caprate and glycerol tris (2-ethylhexanoate) and is suitable for use for a wide range of automotive, household and industrial applications.

23 Claims, 2 Drawing Sheets

*Table 1*

| Propylene glycol dicaprylate/caprate | Glycerol tris 2-ethylhexanoate | Grams<br>Propylene glycol dicaprylate/ caprate | Grams<br>Glycerol tris 2-ethylhexanoate |
|---|---|---|---|
| 20% | 80% | 5.67 | 22.68 |
| 25% | 75% | 7.09 | 21.26 |
| 30% | 70% | 8.51 | 19.85 |
| 35% | 65% | 9.92 | 18.43 |
| 40% | 60% | 11.34 | 17.01 |
| 45% | 55% | 12.76 | 15.59 |
| 46% | 54% | 13.05 | 15.31 |
| 47% | 53% | 13.33 | 15.03 |
| 48% | 52% | 13.61 | 14.75 |
| 49% | 51% | 13.90 | 14.46 |
| 50% | 50% | 14.18 | 14.18 |
| 51% | 49% | 14.46 | 13.90 |
| 52% | 48% | 14.75 | 13.61 |
| 53% | 47% | 15.03 | 13.33 |
| 54% | 46% | 15.31 | 13.05 |
| 55% | 45% | 15.59 | 12.76 |
| 60% | 40% | 17.01 | 11.34 |
| 65% | 35% | 18.43 | 9.92 |
| 70% | 30% | 19.85 | 8.51 |
| 75% | 25% | 21.26 | 7.09 |
| 80% | 20% | 22.68 | 5.67 |

FIGURE 1

*Table 2*

| Solvent | Molecular Weight | Specific Gravity | Vapor Pressure mm Hg at 70°F | Freezing Point (°F) | Flash Point Closed Cup (°F) | Ecotoxic | Eye | Carcinogen IARC |
|---|---|---|---|---|---|---|---|---|
| Methylene Chloride | 84.93 | 1.32 | 349 | -142.06 | none | Ecotoxic | Irritant | Yes |
| Isopropyl Alcohol | 60.1 | 0.7864 | 33 | -127.30 | 53 | No | Irritant | No |
| Inventive Solvent | 470 | 0.9374 | 0.0075 | -100.00 | 400 | No | No | No |
| Di(ethyl glycol) butyl ether | 162.23 | 0.967 | 30 | -90.00 | 212 | Ecotoxic | Severe | Not determined |
| Propylene Glycol | 76.1 | 1.038 | 0.04 | -76.00 | 214 | No | Minimal | No |
| Perchloroethylene | 165.82 | 1.6 | 14.2 | -8.40 | none | Ecotoxic | Burns | Yes |
| Water | 18.02 | 1.0 | 18.96 | 32.00 | none | No | No | No |

FIGURE 2

NON-LETHAL TEMPORARY INCAPACITATION FORMULATION AND NOVEL SOLVENT SYSTEM

FIELD OF THE INVENTION

The present invention is directed to non-lethal formulations for temporarily incapacitating a target and a novel solvent system for the same. The invention is more particularly directed to non-lethal formulations using the solvent system having increased incapacitation times without long term or permanent side effects.

The invention further relates to a novel non-toxic, non-carcinogenic, non-flammable solvent system useful over a wide range of operating conditions and particularly suitable for use in aerosol and other spray devices allowing a highly stable spray.

BACKGROUND OF THE INVENTION

Non-lethal weapons are designed to incapacitate the target, and when properly used do not result in any injuries, fatalities or after effects. Non-lethal weapons in the form of aerosol sprays capable of temporarily incapacitating a target have shown great use both for enforcement and defensive purposes. These non-lethal sprays are particularly useful in close proximity encounters, such as breaking up a bar fight or intervening in a domestic disturbance; stopping fleeing suspects; in hostage or terrorist situations; in barricade situations, where the subject is violent, but has not taken a hostage; and generally in crowd control or riot situations.

Aerosol sprays commercially available are of three types: chloroacetophenone (CN) commonly known as mace, orthochlorobenzylidenemalononitrile (CS) commonly known as tear gas, and oleoresin capsicum (OC) also known as pepper spray. Both mace and tear gas are lachrymators that cause tearing and irritation. However, they have no effect on those who are enraged or are under the influence of narcotics, or alcohol. Pepper sprays contain an extract of hot pepper and act as an inflammatory agent causing closing of the eyes and coughing.

Initial aerosol type formulations were of the lachrymator type, such as Chemical Mace® lachrymator, included various types of liquid based CN chemical formulae in pressurized aerosol spray containers. However, the lachrymator agents used in such sprays contain highly toxic and/or cancer causing chemicals. Furthermore, such technology used environmentally unfriendly carrier agent/solvents such as trichlorotrifluoroethanes (CFC's 111, 113) and cosmetic kerosene.

In an effort to overcome these problems, a pepper based inflammatory spray technology was developed and first introduced through the CAP-STUN® brand pepper spray in 1982 introduced into the self-protection market. Pepper sprays are available with various concentration of capsaicin (capsaicinoids), which is the primary ingredient producing the effects of pepper spray. Various types of pepper sprays have since come into existence; however, the technology of pepper spray is still basically unchanged since its inception.

Even though pepper sprays and other lachrymators are generally effective for self-defense purposes, improvements are still desired, particularly in decreasing the time it takes for incapacitation of the recipient and increasing the length of time for incapacitation while avoiding long term effects on the target. Law enforcement officials would like to be able to incapacitate a suspect for a sufficient time to allow immobilization and/or transport to an appropriate holding facility. Thus, efforts have been made to increase effectiveness or duration of the pepper spray by increasing the amount of pepper in the spray. However, this has been limited by the need to avoid permanent harm or injury to the recipient, particularly damage to the eyes, skin, or upper respiratory tract. This has left unmet the need for a more effective and longer duration spray that can be used without long-term harm to the recipient, while reducing or eliminating any impact on the user and any bystanders, and reducing any adverse effects on the environment.

Another problem with the pepper sprays and other lachrymators dispensed using an aerosol or other spray dispensing system is that when it is dispensed, there is always the possibility that an open flame or other source of ignition may be present that could ignite the solvent or carrier of the mixture resulting in serious bodily harm to both the user and the intended recipient of the lachrymator. Examples of some possible sources of ignition include lit cigarettes or cigars, burning candles or matches, and stoves or other heating devices.

In particular, alcohol-based or containing sprays pose a considerable risk of ignition. However, replacing the alcohol cannot simply be replaced with water since the active ingredients are not soluble therein and thus an additional solubilizing agent must be used—most of which also exhibit flammable tendencies.

Foam based carrying agents also may potentially cause gagging, vomiting and choking from entry of foam bubbles in the respiratory system. Chlorinated solvents such as CFC's, HCFC's and HFC's can be damaging to the eyes as well as to the environment.

There are a number of household and industrial aerosol and other spray device propellant and solvent formulations currently available. Known nonflammable carriers, although less likely to ignite when exposed to such sources of ignition, pose their own problems. Many are classified as carcinogenic, and thus are not suitable for use where there is skin contact. Most are as ozone depleting and fail to meet applicable standards for ozone depletion and volatile organic compound (VOC) emissions.

Due to the self-pressurized nature of aerosols and the direct correlation between pressure, temperature and volume, extreme temperature variance is an area of concern. Particularly desirable aerosols must be capable of operating even when exposed to high temperatures, such as in a parked car in the summer, and also be functional when the temperature falls below zero. Those solvents that don't thicken and freeze, such as hydrocarbons and alcohols, are generally flammable. Exposure to extreme elevated temperatures can cause instability of the spray pattern while exposure to sub-zero temperatures can freeze the formulation and render the system inoperable.

Another area of concern, particularly where irritating chemicals are being sprayed, is the ability to reliably direct the spray to an intended target and not have it remain airborne for extended periods of time. When used indoors, many sprays can remain airborne too long, thus affecting bystanders, further circulating into the heating or air conditioning system, and contaminating other areas. When used outdoors, many sprays can be blown back to the face of the user or more erratically with wind direction and contaminate bystanders rather than the intended target. Furthermore, prior art sprays have had difficulty in penetrating rain, and thus have not been able to reach their desired target when used in such conditions.

Other problems arise with defense spray applications, such as in pepper sprays and mace, where the spray is directed to the facial area. Here the solvent formulation requirements are stricter since they are intentionally sprayed on an individuals face, with exposure to eyes, skin and the respiratory system. Therefore, the solvent formulation should also pass toxicological tests showing no damage to the eyes, skin or upper respiratory tract. Furthermore, the solvent formulation must be miscible with the active ingredients in the defense spray.

Prior art solvent systems have proven unsuitable for application due to a number of problems including flammability, toxicity, carcinogenic properties, irritant, adverse reactions with materials contacted, and inability to dissolve and maintain in a dissolved state the active ingredient. Furthermore, known solvents that are non-toxic when used in an aerosol dispensing system lack the ability to be readily controlled and directed, particularly in windy and/or rainy conditions.

SUMMARY OF THE INVENTION

It has now been discovered that non-lethal formulations using the novel solvent system of the present invention exhibit an increased effectiveness and duration of temporary incapacitation of the target while remaining non-toxic, non-hazardous, non-flammable, highly-stable, environmentally safe and able to withstand extreme operating temperatures. The non-lethal, temporarily incapacitating formulation and the solvent system when used as an aerosol substantially eliminates blow back on the user and has a spray pattern that is stable and controllable even in windy conditions. The formulation and solvent system are also suitable for use with other spray applications and non-aerosol pressurized delivery systems. Furthermore, the novel solvent system of the present invention has also been found to be useful in a wide range of applications including use in automotive, industrial, household and insecticide applications. For example, the novel solvent system is suitable for use with oil based active ingredients including resins, cosmetics, foods, tear gases, pepper based products, pharmaceuticals, skin care preparations, sunscreen products, antiperspirants, bath oils, food additives, automotive products, household products, industrial products, insecticides, paints, and veterinary products, and the like.

The solvent system is a mixture of propylene glycerol dicaprylate/caprate and glycerol tris (2-ethylhexanoate) so that the solvent has a molecular weight of at least 100, preferably between about 100 to about 500, and a vapor pressure of less than 5 mm Hg. The ratio of the weight of propylene glycol dicaprylate/caprate to the weight of glycerol tris (2-ethylhesanoate) in the formulation can range from about 20:80 to 80:20, preferably from about 45:55 to about 55:45, and most preferably is about an equal mixture.

The solvent system is particularly well suited for aerosol applications with the use of any appropriate propellant such as carbon dioxide or nitrous oxide, and for other spray applications with any appropriate propellant also including nitrogen.

The non-lethal, temporarily incapacitating formulation allows the ready dispersion of active ingredients including oil-based inflammatory agents, such as those in the capsaicin family, to readily dissolve, thus allowing the use of lower concentrations of capsaicins and/or increasing the effectiveness of the spray. The non-lethal formulation of the present invention results in shorter times being required for the target to become incapacitated as well as a longer duration of incapacitation than possible with known conventional pepper sprays and lachrymator sprays.

According to an embodiment of the invention, the incapacitating agent is present in an amount of about 0.18% to about 3% by weight of the solvent system. According to another embodiment of the invention, the incapacitating agent is present in an amount of about 1.4% to about 1.5% by weight of the solvent system.

BRIEF DESCRIPTION OF THE DRAWINGS

FIG. 1 is Table 1 showing the solvent system of the present invention with various ratios of components.

FIG. 2 is Table 2 comparing properties of the solvent system of FIG. 1 to known solvents.

DETAILED DESCRIPTION OF THE INVENTION

It has now been discovered that the non-lethal formulation of the present using the novel solvent system of the present invention is not only more effective than prior art formulations at lower concentrations of capsaicins, but does so without lasting or toxic effects on the recipient. Furthermore, due to the unique characteristics of the solvent system, use in an aerosol or other spray or pressurized delivery system allows targeting of the spray without blowback on the user, even indoors or in windy conditions outdoors.

Furthermore, the novel solvent system of the present invention has also been found to be useful in a wide range of applications including use in automotive, industrial, household and insecticide applications. For example, the novel solvent system is suitable for use with oil based active ingredients including resins, cosmetics, foods, tear gases, pepper based products, pharmaceuticals, skin care preparations, sunscreen products, antiperspirants, bath oils, food additives, automotive products, household products, industrial products, insecticides, paints, and veterinary products, and the like.

Solvent System

The solvent system of the present invention has several physical and chemical properties that make this product significantly more stable and suitable for use for a broad range of applications. Furthermore, the solvent system of the present invention is non-toxic, non-carcinogenic, has a wide operating temperature range throughout which it maintains its stability. Also the solvent system readily dissolves and solubilizes oil based active ingredients while remaining non-flammable and without becoming corrosive to the environment or to people or animals. The solvent system is safe for skin contact and in fact can be used with pharmaceutical and skin care preparations. Additionally, when used in an aerosol or spray formulation, its unique characteristics produces more stable aerosol or other type of spray, that is controllable in rainy and windy conditions and less likely to contribute to prolonged airborne contamination or blow back due to windy conditions.

In particular, the solvent system has a significantly greater average molecular weight of 470 mw in comparison to the prior art solvents water at 18.02 mw or isopropyl Alcohol at 60.1 mw. The solvent system also has a significantly lower vapor pressure of 0.0075 mmHg (70° F.) in comparison with water at 18.96 mmHg and isopropyl alcohol at 33 mmHg. This unique combination of various physical and chemical factors in the solvent reduces the possibility of airborne chemical to vaporize eliminating the possibility of contamination of indoor area or bystanders resulting in a stable chemical during aerosol application in windy conditions, with minimal possibility of chemical blow back on user.

The solvent system of the present invention comprises a mixture of propylene glycol esters of short chain fatty acids and glycerol tris 2-ethylhexanoate.

Propylene glycol esters of short chain fatty acids are the propylene glycol mono- and diesters of caproic, capric, caprylic and lauric acid and their mixtures like propylene glycol dicaprylate/dicaprate is a commonly used mixture of the propylene glycol diesters of caprylic (C8) and capric (C10) acids. They are very similar to other propylene glycol esters of fatty acids and to their triglycerides. These materials are neutral, nearly colorless and odorless esters with very low cloud points.

Propylene glycol fatty acid esters are widely used in the pharmaceutical, cosmetics and food industries. Pharmaceutical applications include use in oral and parenteral products as vehicles and solvents. In the cosmetics industry, propylene glycol esters of fatty acids are used in skin care preparations, sunscreen products, antiperspirants, pre-shave emulsions and bath oils, mainly as emollients. These esters are approved as food additives in various applications, mostly as emulsifiers, stabilizers or fat replacements.

Glycerol tris (2-ethylhexanoate), a colorless to pale yellow, transparent oily liquid with negligible odor, is used mainly as an emollient in a range of personal care preparations. It is not approved for use in either pharmaceutical preparations or in food applications.

The propylene glycol esters of short chain fatty acids component used in the present invention is preferably propylene glycol dicaprylate/caprate. Propylene glycol dicaprylate/caprate has the Chemical Abstracts Registry Nos. CAS: 58748-27-9; 9062-04-8; and 68988-72-7 and is a mixture of the propylene glycol diester of caprylic acid and the ester of capric acid. The propylene glycol dicaprylate/caprate is a liquid with a boiling point greater than 200° C., a cloud point of −40° C., a flash point of 185° C. and a vapor pressure less than 1 hPa at 20° C. The density is 920 kg/m3 and the viscosity is 10 m Pa.s. Although not soluble in water, it is soluble in many organic solvents.

Suitable sources of propylene glycol dicaprylate/caprate are well known to those in the cosmetic industry and include Capital City (Capex 200), Henkel (Edenol 302), Hodag (Hodag CC-22), Inolex (Lexol PG 855, Lexol PG 865), Lipo (Liponate PC), Hüls America (Migloyol 840), Stepan (neobee M-20), Trivent (Trivent PG-D), and UPI (Unitolate 380).

The glycerol tris 2-ethylhexanoate component is also known as trioctanoin and has the Chemical Abstracts Registry No. CAS: 7360-38-5. Glycerol tris 2-ethylhexanoate is the triester of glycerin and 2-ethylhexanoic acid. Glycerol tris-2-ethylhexahoate has similar properties, with a slightly higher flash point of 200° C., a slightly higher density of 950 kg/m3 and a much greater viscosity of 30 m Pa.s.

Care should be taken not to confuse glycerol tris 2-ethylhexanoate with glycerol trioctanoate, also known as glycerol tricaprylate or tricaprylin. Glycerol tris 2-ethylhexanoate is C8 branched and used almost exclusively in personal care preparation, while glycerol trioctanoate is C8 linear with a wide range of applications.

Suitable sources of glycerol tris 2-ethylhexanoate are well known to those in the cosmetic industry and include Kyoei (Hexalan), Nikko (Nikko Trifat S-308) Nisshin Oil Mills (Nomcort T.I.O.) and Trivent (Trivent OC-G).

The solvent system is made by simply mixing together the two components using any suitable means known to one of skill in the art. No special equipment is needed as the two components are readily miscible.

In the solvent system, the ratio of propylene glycerol dicaprylate/caprate to glycerol tris/2-ethylhexanoate is preferably in a range from about 20:80 to 80:20; and more preferably in a range from about 45:55 to about 55:45 by weight. In the most preferred embodiment of the present invention, the two components of the solvent system are present in about equal amounts by weight. If these ratio falls beyond the mentioned range the solvent may either freeze due to change in freezing point, become flammable due to change in flash point, or not remain stable in windy condition due to change in vapor pressure and surface tension.

The novel solvent system of the present invention is a colorless and transparent liquid that is both odorless and tasteless. The solvent system usually has a viscosity of 35 centipoise zmeasured by using Brookfield RVT viscometer with spindle #3 at 60 RPM.

The solvent system of the present invention was developed to withstand an extreme range of operating conditions. It has a cloud point (temperature where the solvent begins to turn cloudy) of −42° C. and a flashpoint of 205° C. This falls well within the non-flammable range for aerosol and spray type applications, even under extreme operating conditions.

The solvent system of the present invention is environmentally safe and readily biodegradable. Testing undertaken has shown that the solvent will undergo rapid and extensive biodegradation in the environment.

Many of the prior art solvent systems also exhibited problems in dissolving, or even suspending, the resinous active ingredients of the pepper spray composition and often requiring excessive agitation for lengthy periods of time. For example, the resinous active ingredients are non-soluble in a water based system. Not only must excess and vigorous mixing be undertaken, but other solvents be added to permit even a limited degree of solubility. Although soluble in alcohol, no trace of water can be present, otherwise separation will occur.

In direct contrast, the solvent system of the present invention exhibits a high degree of oil solubility enabling it to solubilize most oily substances at both low and higher concentrations, i.e. from about 0.05% to about 30% by weight of an oil based active ingredient is readily solubilized in the novel solvent of the present invention. For example, oleoresin capsicum rapidly dissolves with minimal agitation and becomes a homogeneous part of the solvent system.

Incapacitating Agent

Any suitable incapacitating agent can be used with the solvent system of the present invention and include those of the inflammatory or irritant type and may be mace, tear gas or a pepper agent. Preferably the incapacitating agent is an inflammatory agent of the pepper type and includes synthetic and natural oleoresin capsicum and capsaicins (including the entire family of capsaicinoids). Suitable incapacitating agents include dibenzoxazepine (CR), chloroacetophenone (CN), ortho-chlorobenzalmalononitrile (CS), oleoresin capscium (OC), oleoresin paprika, paprika, capsicums (chili peppers), trans-8-methyl-N-vanillyl-6-nonenamide (capsaicin), 8-methyl-N-vanillyl-nonamide (dihydrocapsaicin), 7-methyl-N-vanillyl-octamide (nordihydrocapsaicin), 9-methyl-N-vanillyl-decamide (homodihydrocapsaicin), trams-9-methyl-N-vanillyl-7-decenamide (homocapsaicin), (3R, 3 þ, 5 þR)-3,3'-dihydroxy-á,k-caroten-6'-one (capsanthin), N-vanillyl-octamide, N-vanillyl-nonamide, N-vanillyl-decanamide, N-vanillyl-undecanamide, N-vanillyl-paaiperic acid amide, and mixtures thereof.

The strength of the non-lethal temporarily incapacitating spray can be adjusted by varying the concentration of the incapacitating agent, such as a capsaicin family member, in the formulation. The strength of the non-lethal temporarily incapacitating spray should be such that it reliably and reproducably produces the desired effect on the target or recipient but not so strong that it induces injury or harm to the target or requires a lengthy recovery time.

For a non-lethal temporarily incapacitating spray of the inflammatory type (i.e., a pepper spray), the target should exhibit immediate closing of the eyes, shortness of breath, and burning sensation of the skin. However, it should not be so strong that it produces excessive redness of the skin and lengthy inflammation requiring a recovery time of more than one hour. It has been found that concentrations of capsaicin below 0.5% are inconsistent in their effects, and thus is not desirable since the user cannot rely upon it being effective when needed. Likewise, capsaicin concentrations above 1.60% have been too strong and require at least an hour for recovery, which again is unacceptable. Concentrations of 0.18% capsaicin have produced documented effectiveness of 60% while concentrations of 0.90% have produced an effectiveness of about 90%. Thus, concentrations between 0.5% and 1.6% are preferred. Within this range, concentrations of 0.5% to 1.00% have been found to be useful for many self-defense applications in that they are stable and consistent in their performance, with the concentration of 1.00% exhibiting 90% to 95% effectiveness. We have discovered that the most preferred level of capsaicin is 1.45% since it is the most potent level that can be delivered without potential hazards. This is particularly important for law enforcement and military applications since we have determined that there is a small population of individuals for which 0.90% concentration does not achieve proper inflammation, but at 1.45% all subjects achieve proper inflammation without excessive recovery time or potential hazards.

Care must be taken when comparing the concentrations used to describe various commercially available pepper sprays since the U.S. Consumer Product Safety Commission's labeling system only refer to the percentage of the oleoresin capsicum relative to the other ingredients in the canister including the carrier, a propellant, and often marking dyes or other chemicals. What the oleoresin capsicum concentration does not measure is the concentration of the active ingredients, i.e. the capsaicin, in the oleoresin capsicum formulation. Thus, the oleoresin capsicum concentration only represents the amount of oleoresin capsicum (oily resin) in a canister and not its strength. The heat or strength of oleoresin capsicum is measured by the quantity of an active ingredient called capsaicin. Therefore, the higher the capsaicin amount, the hotter the oleoresin capsicum.

Capsaicin is the ingredient within the oleoresin capsicum that causes inflammation of mucous membranes. The reason some peppers are hotter than others is due to the amount of capsaicin. The percentage of capsaicin will vary depending on the pepper species, the geographical origin of the pepper and climatic growth conditions as well as upon oleoresin extraction and formulation processes. Thus, one must consider the amount of the capsaicin within the oleoresin capsicum as well as the oleoresin capsicum concentration to determine the amount of the capsaicin.

A misconception exists that the heat of a pepper spray is best demonstrated through Scoville Heat Units (SHU). SHU testing is none other than "tongue" tasting of the oleoresin capsicum by a panel of 5 individuals. SHU therefore depends on the subjective taste experience of the panel and is not accurate since it depends on the individual taste sensitivity which changes from person to person and does not measure the actual chemical percentage within the product. Although the SHU test is an appropriate test for the food spice community, it cannot serve as the standard for oleoresin capsicum spray formulations where the user depends on the oleoresin capsicum's consistent and reliable performance.

Accordingly, to scientifically measure the amount of Capsaicin within oleoresin capsicum sprays, High Pressure Liquid Chromatography (HPLC) is used to obtain exact and accurate machine data. HPLC provides an acceptable international guideline for testing the capsaicin amount by the scientific community. One skilled in the art is familiar with the procedures for such measurement. See, for example, the Official Analytical Methods of The American Spice Trade Association (HPLC method 21.1).

Propellant

Various propellants can be mixed with the solvent or formulation in order to place it under pressure so that the solvent or formulation can be dispensed as a spray. Any suitable propellant known to one of skill in the art can be used and will depend upon the particular application, the environmental effects the pressurized container will be subjected to, the size of the container, the desired range, and the like. The propellant should be able to maintain an adequate pressure and avoid over-pressurization at the desired operating temperature range.

Some propellants can vary their pressure in response to a change in the temperature. For example, isobutane and propane increase in pressure with an increase in temperature and nitrogen decreased pressure as the temperature drops. Although these propellants can be used, care must be taken. If such an aerosol is stored inside a car during hot seasons the internal pressure can rise to cause deformation of the canister body and bursting. On the other hand when temperature fall during cold season, the aerosol may loose its delivery range due to loss of pressure.

A particularly preferred propellant is carbon dioxide ($CO_2$) (CAS: 124-38-9) due to its highly desirable properties. $CO_2$ is colorless, odorless and noncombustible, and its pressure remains relatively unaffected by extreme temperatures. Furthermore, $CO_2$ evaporates instantly upon contact with the environment outside the spray device as it exits the valve opening or nozzle orifice. Thus, $CO_2$ simply created initial propulsion to launch the liquid formulation to the target and does not travel with the solvents to the target. This avoids the need to consider the effects of the propellant on the intended target or recipient of the spray.

Another propellant suitable for wide range of operating temperatures is nitrous oxide and is desirable for the same reasons as carbon dioxide.

The propellants can be used in any amount known to one of skill in the art to be suitable for pressurizing the solvent. In a preferred embodiment of the present invention, the propellant is present in an amount between 1 to 30% by weight as a pressurizing agent in the solvent resulting in a stable environment with none or minimal loss of pressure. For example, a starting pressure of 120 psi requires the use of about 4 to 5% $CO_2$ by weight to be introduced into the container holding the solvent mixture.

Although nitrogen is not suitable for small aerosol containers due to its loss of pressure with each spray and a concomitant decrease in the range with each spray, it is suitable for use with other pressurized delivery systems and in large pressurized systems.

The solvent system can also be used in other delivery systems such as fire extinguisher size canisters, larger pressurized tanks, ammunitions capable of delivery of chemical payloads, paint pellet guns, vehicle capable of delivering chemicals and aircrafts capable of chemical dissemination from air with any necessary and appropriate propellant or pressurizing agent.

Accordingly, one of skill in the art would be able to readily determine the appropriate propellant or pressurization agent for use with the solvent depending upon the desired application, the desired range, the active ingredient, the size of the container, the operating conditions, and the other factors influencing choice of propellant that one of skill in the art is familiar with.

EXAMPLES

The following examples will serve to illustrate the novel features and advantages of the present invention. While these examples will show one skilled in the art how to operate within the scope of this invention, they are not to serve as a limitation on the scope of the invention for such scope is only defined in the claims below.

The first set of examples is directed to making of the novel solvent system and the improved properties of these novel solvent systems. The second set of examples is directed to the use of the novel solvent system in a novel aerosol or spray type of system. The improved properties of the aerosol, such as hang time, is readily shown by the examples. The third set of examples shows the improved and novel pepper spray formulations of the present invention and their improved properties. Various characteristics of the solvent system of the present invention were tested and the results are set forth below.

Example 1

Preparation of Solvent System

Propylene glycol dicaprylate/caprate in the weight in grams noted in Table 1 below was mixed with glycerol tris 2-ethylhexanoate in the weight in grams noted to yield a solvent system having a viscosity of 33 centipoise and a specific gravity of 0.9374. The components were each measured and then placed in a one ounce or 28.35 gram net weight container and mixed together with minor agitation. The results are set forth in Table 1 of FIG. 1.

The solvent system was compared to other known solvents as set forth in Table 2 in FIG. 2.

Example 2

Propellant/Solvent System

The procedures of Example 1 were followed with the additional step of introduction of a propellant via pressure in the canister in aliquots with shaking prior to introduction of the next aliquot until the indicated amount of propellant was introduced into the solvent system. The amounts and results are set forth in Table 3 below.

TABLE 3

| Propylene glycol dicaprylate/caprate | Glycerol tris 2-ethylhexanoate | $CO_2$ or Other Propellants | Propellant Grams |
|---|---|---|---|
| 18% | 78% | 4% | 1.13 |
| 23% | 73% | 4% | 1.13 |
| 28% | 68% | 4% | 1.13 |
| 33% | 63% | 4% | 1.13 |
| 38% | 58% | 4% | 1.13 |
| 43% | 53% | 4% | 1.13 |
| 44% | 52% | 4% | 1.13 |
| 45% | 51% | 4% | 1.13 |
| 46% | 50% | 4% | 1.13 |
| 47% | 49% | 4% | 1.13 |
| 48% | 48% | 4% | 1.13 |
| 49% | 47% | 4% | 1.13 |
| 50% | 46% | 4% | 1.13 |
| 51% | 45% | 4% | 1.13 |
| 52% | 44% | 4% | 1.13 |
| 53% | 43% | 4% | 1.13 |
| 58% | 38% | 4% | 1.13 |
| 63% | 33% | 4% | 1.13 |
| 68% | 28% | 4% | 1.13 |
| 73% | 23% | 4% | 1.13 |
| 78% | 18% | 4% | 1.13 |

Example 3

Active Ingredient/Solvent System

The procedures of Example 1 were followed with the additional step of introduction of an active ingredient (capsaicin) into the container prior to the minor agitation step. The amounts and results are set forth in Table 4 below.

TABLE 4

| Propylene glycol dicaprylate/caprate | Glycerol tris 2-ethylhexanoate | Active Ingredients |
|---|---|---|
| 19.28% | 79.28% | 1.45% |
| 24.28% | 74.28% | 1.45% |
| 29.28% | 69.28% | 1.45% |
| 34.28% | 64.28% | 1.45% |
| 39.28% | 59.28% | 1.45% |
| 44.28% | 54.28% | 1.45% |
| 45.28% | 53.28% | 1.45% |
| 46.28% | 52.28% | 1.45% |
| 47.28% | 51.28% | 1.45% |
| 48.28% | 50.28% | 1.45% |
| 49.28% | 49.28% | 1.45% |
| 50.28% | 48.28% | 1.45% |
| 51.28% | 47.28% | 1.45% |
| 52.28% | 46.28% | 1.45% |
| 53.28% | 45.28% | 1.45% |
| 54.28% | 44.28% | 1.45% |
| 59.28% | 39.28% | 1.45% |
| 64.28% | 34.28% | 1.45% |
| 69.28% | 29.28% | 1.45% |
| 74.28% | 24.28% | 1.45% |
| 79.28% | 19.28% | 1.45% |

Example 4

Subzero Climatic Operation

The solvents from Example 1 were tested and found to have a cloud point of −40° C. where the solvent became cloudy and lost its transparency. In order to determine realistic cold operating temperatures, the solvents from Example 1 were placed in sub zero temperatures for a pre-determined time and then further evaluated it for its viscosity.

At room temperature, the solvent has a viscosity of 35 centipoise as measured using a Brookfield RVT Viscometer with Spindle #3 at 60 RPM.

In this test, three identical solvent samples were each placed in a glass container, which was then placed in a laboratory type freezer for a period of 48 hours with the first at a temperature of −5° C., the second at −20° C. and the third at −30° C. Immediately upon removal from the freezer, the samples were tested and all exhibited a viscosity of approximately 35 centipoise. Since the viscosity did not change even after 48 hours of subzero temperatures, it is suitable for use in freezing climates.

The same test was conducted using a solvents disclosed in U.S. Pat. No. 5,217,708 to Defense Technology Corporation of America, namely, a mixture of Propylene Glycol 5%, SDA40B alcohol 35% and distilled water 50%. This prior art solvent froze at −10° C. and became inoperative in a 24 hour freeze test due to its high volume of water.

Example 5

Solubility

The solubility of the solvents with various active ingredients was tested using two different types of test assays. In the first procedure, the active ingredient was placed inside a test tube and solvent was added at 10/90, 20/80, 30/70, 40/60 and 50/50 ratios of active ingredient to solvent. The test tube was then shaken by hand a few times and let stand for observation. In the second procedure small amount of ingredients were placed on the slide and observed under a microscope as one milligram of solvent was introduced on the slide. Once again the reaction of solvent and ingredients were observed.

The solvent in both procedures disintegrated and dissolved the active ingredients into a homogenous unit within less than 60 seconds at room temperature of 70° F.

The ingredients tested included capsaicin crystals, oleoresin capsicum, mineral oil, vegetable oil, various oleoresins including paprika, ginger, eucalyptus, onion, ginger, lime, clove, mustard, and horseradish, as well as various natural waxes and esters.

A similar test with solvent made in accordance with the solvent disclosed in U.S. Pat. No. 5,217,708 to Pinkney comprising 5% propylene glycol, 35% SDA40B alcohol, and 50% distilled water. This solvent failed to dissolve any of the oil based active ingredients due to its water soluble characteristics.

Solubility in Seconds

Solubility Analysis

| Solvent | Mixture Ratio | Test Tube Result | Slide Result |
|---|---|---|---|
| Inventive Solvent | 10/90 | <10 Seconds | <5 Seconds |
| Inventive Solvent | 20/80 | <10 Seconds | <5 Seconds |
| Inventive Solvent | 25/75 | <10 Seconds | <5 Seconds |
| Inventive Solvent | 30/70 | <10 Seconds | <5 Seconds |
| Inventive Solvent | 35/65 | <10 Seconds | <5 Seconds |
| Inventive Solvent | 40/60 | <10 Seconds | <5 Seconds |
| Inventive Solvent | 45/55 | <10 Seconds | <5 Seconds |
| Inventive Solvent | 50/50 | <10 Seconds | <5 Seconds |
| Inventive Solvent | 55/45 | <10 Seconds | <5 Seconds |
| Inventive Solvent | 60/40 | <10 Seconds | <5 Seconds |
| Inventive Solvent | 65/35 | <10 Seconds | <5 Seconds |
| Inventive Solvent | 70/30 | <10 Seconds | <5 Seconds |
| Inventive Solvent | 75/25 | <10 Seconds | <5 Seconds |
| Inventive Solvent | 80/20 | <10 Seconds | <5 Seconds |
| Inventive Solvent | 90/10 | <10 Seconds | <5 Seconds |
| Solvent (Patent: 5,217,708) | AS IS | Not Soluble | Not Soluble |

| List of Ingredients Tested |
|---|
| Capsaicin crystals |
| Dihydrocapsaicin crystals |
| Oleoresin Capsicum |
| Mineral Oil |
| Vegetable Oil |
| Oleoresins paprika |
| Oleoresin ginger |
| Oleoresin eucalyptus |
| Oleoresin onion |
| Oleoresin lime |
| Oleoresin clove |
| Oleoresin mustard |
| Oleoresin horseradish. |
| Natural waxes |
| Natural esters |

Example 6

Material Contamination, Stain and Odor

The solvents of Example 1 were tested on various surfaces in order to evaluate its contamination level. 10 cc of solvent was poured then rubbed on following surfaces then examined for appearance, odor and stain. It was then further reviewed under microscope for any unusual appearance.

In all tests performed the solvent did not produce an odor, damage the surface or leave a stain. The excess was easily wiped with a water damp cloth.

The surfaces and materials evaluated included nylon fabrics, cotton fabrics, vinyl surfaces, wood with polish and no urethane, wood with polish and urethane, aluminum, steel, copper, silver, gold, various plastics, various rubbers, leather, wool fabric, silk, an oil based painted surface and water-based painted surface.

In contrast similar test with isopropyl alcohol solvent did remove some wood polishes and dulled vinyl surfaces, some plastics, leather and water based painted surfaces.

Example 7

Indoor Contamination

Several pepper solutions were made by mixing the solvents of Example 1 with capsaicin at 1% and 2% oleoresin capsicum at 5% and 10% was added to the solvents. These ingredients used in pepper sprays were selected because of their excessive pungency and immediate burning sensation of mucous membranes. The pepper solvent solution was then pressurized in an aerosol container to 30, 50, 80, and 120 psi.

These solutions were each tested by spraying them for one, two and three seconds into a closed area of 5 feet×5 feet×8 feet, similar to a small elevator. Within less than 10 seconds after spraying, a volunteer entered into this chamber without any protective device and remained for five minutes. The volunteer was removed from the chamber and evaluated for any discomfort associated with pepper spray ingredients such as irritation of eyes, sneezing, shortness of breath, and coughing.

Each volunteer was observed immediately upon exit from the chamber, and then after one hour and after 8 hours from entrance into the chamber. None of the volunteers showed any symptoms associated with pepper sprays.

This demonstrated the solvent is a unique characteristic to contain the active ingredients due to its surface tension and viscosity without misting and aerosolizing the ingredients into the environment causing contamination. Therefore the solvent can be used to deliver the ingredients in a target specific manner directly to the target.

A comparison test was conducted using isopropyl alcohol solvent. The isopropyl alcohol solvent produced a highly irritating atmosphere with airborne capsaicin. One could not enter the enclosure without wearing proper respirator masks and proper filtration.

Example 8

Wind Penetration

The stability of liquid projectile of the solvent system of the present invention while airborne was tested. This was assessed by placing the solvent in an aerosol form and then projecting the aerosolized solvent towards a targeted upper body of specially designed mannequin from a distance of 10 feet. An industrial and customized fan with approximately 2 feet in diameter was used to generate various wind speeds. A wind meter was used to log the speed.

The fan was placed in three different pre-selected positions. In position (a) the fan was directly facing the spray and spraying into wind. Position (b). was the back of the spray (tail wind). Position (c) was at a 90 degree angle or cross wind, to the spray to assess side wind. The fan generated speeds of 5, 10, 15, 20, 30, 40, 45 miles per hour for each of the three positions.

In all tests combination up to 40 mile per hour, the liquid reached the target successfully, however above 40 mile per hour in position (a) and (c) only 80% of spray reached the target and the remaining 20% was forced by wind to follow its route thus showing that the liquid is highly stable in windy conditions with no effect on bystanders.

A comparison test was conducted using an isopropyl alcohol solvent, where the spray was adversely impacted for all positions at fan speeds below 5 miles per hours.

Example 9

Toxicology

The solvent blend and capsaicinoids mixture at a concentration of 1.45% capsaicin underwent independent toxicological testing with the following findings:

Eye Irritation: When tested the formula was not considered to be an eye irritant per Eye Irritation test method of US Federal Hazardous Substance Act.

Inhalation: When tested the formula was non-toxic to the test animals at the maximum concentration that could be generated with the test system per Acute Inhalation Toxicity Test method.

Allergy: When tested the formula did not to cause an allergic reaction as tested per Kligman Skin Sensitization method of US Federal Hazardous Substance Act. There were no significant differences in skin irritation observed in the test animals and control animals.

Example 10

Effectiveness

The solvents were mixed with capsaicin and undergoing various tests in order to establish its effectiveness. Various concentrations of cap saicin were used including; 0.92%

1.10% 1.30%, 1.45%, 1.50%, 1.70%, 2.00%. The concentrations were independently verified by High Pressure Liquid Chromatography equipment.

One milligram of the solution was placed on the tongue, inside the nostrils, near the eyes at tear duct and on the skin.

It was determined that capsaicin at and above 1.70% produces excessive redness and inflammation of mucous membranes lasting up to two hours. This duration of time is in drastic excess of what is required by military and police officers in order to subdue or arrest an individual. Therefore further testing at above these levels were not pursued.

As the concentration increased above the 0.92% level the duration of recovery prolonged and the inflammation of mucous membranes intensified.

To assess the superiority of this solvent for delivery of capsaicin, we tested the new solvent at 0.92% capsaicin and compared its results to a solution of anhydrous isopropyl alcohol at 0.92% capsaicin, which is same exact formula as CAP-STUN® brand used more than a decade exclusively by Federal Law Enforcement and the founder of pepper spray. The solvent was aerosolized at 10 feet toward facial area of volunteers.

The differences of effects were drastic. The eyes shut instantly with the new solvent as its unique characteristic of molecular weight and viscosity deposited in a focus manner the capsaicin into the eyes. With the alcohol formula on the other hand the spray misted and evaporated prior to hitting the eyes and excess capsaicin was left airborne and partially deposited into the targeted eyes. The eyes eventually shut.

Because of this focus delivery of the entire amount of capsaicin to the target, the new solvent produced excessive mucous discharge from the nose followed by an extremely intense burning sensation of the skin. In contrast alcohol solvent produced minimal discharge from the nose and the burning sensation although present is not as intense as with the novel formulation of the present invention while water based formulations result in just a mild burning sensation to the skin. Furthermore, the novel solvent of the present invention instantaneously causes closing of the eyes upon impact while alcohol has a slight delay and water based formulations have an excessive delay.

The recovery period was different as with alcohol solvent the subject was capable of opening the eyes in less than 15 minutes. With the new solvent the eyes were shut up to a maximum of 25 minutes.

Example 11

Environmental Impact

The solvents made according to Example 1 were tested using the Sealed Vessel Test, a $CO_2$ production test based on OECD Guideline 301B. The test system is closed and is suitable for determining the ready and ultimate biodegradability of liquid substances.

The solvents underwent rapid and extensive biodegradation in the simulated environmental exposure and thus were found to be environmentally safe and readily biodegradable.

Example 12

Pepper Spray Formulation

A pepper spray formulation in accordance with the present invention was made in a one-ounce net weight aerosol spray container as follows:

| | |
|---|---|
| Net Weight: | 1.00 ounce (28.35 grams) |
| Capsaicinoids: | 1.45% measured by High Pressure Liquid Chromatography |
| Capsaicinoids potency: | 15 million SHU purity |
| Solvent ratio: | Mixed equally at 46.50% |
| CO2: | 4.50% with starting pressure of 120 psi |
| Viscosity: | 33 Centipoise |
| Density or Specific Gravity: | 0.9374 |
| Canister internally lining: | Epoxy Phenolic |
| Canister pressure: | To withstand internal pressure of 270 psi |
| Valve stem gasket material: | Hex Buna |

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

That which is claimed is:

1. A method for incapacitating a subject, comprising:

providing a non-lethal temporarily incapacitating formulation suitable for use in an aerosol or spray application, the incapacitating formulation comprising a solvent system comprising a mixture of propylene glycol esters of short chain fatty acids and glycerol tris (2-ethylhexanoate); and an incapacitating agent; and applying the non-lethal temporarily incapacitating formulation into the facial area of the subject.

2. The method of claim 1 wherein said applying comprises spraying the non-lethal temporarily incapacitating formulation into the eyes of the subject.

3. The method of claim 1, wherein the non-lethal temporarily incapacitating formulation further comprises a propellant.

4. The method of claim 3 wherein said propellant is miscible in said solvent system.

5. The method of claim 4 wherein said propellant is carbon dioxide.

6. The method of claims 1 wherein the propylene glycol esters of short chain fatty acids is propylene glycol dicaprylate/caprate.

7. The method of claim 6 wherein the propylene glycol dicaprylate/caprate is present in an amount of 20 to about 80% by weight of the solvent system.

8. The method of claim 6 wherein the propylene glycol dicaprylate/caprate is present in an amount of 45 to about 55% by weight of the solvent system.

9. The method of claim 1 wherein the glycerol tris (2-ethylhexanoate) is present in an amount of 20 to about 80% by weight of the solvent system.

10. The method of claim 6 wherein the solvent system comprises approximately equal amounts of the propylene glycol dicaprylate/caprate and glycerol tris (2-ethylhexanoate).

11. The method of claim 1, wherein the incapacitating agent is an inflammatory agent.

12. The method of claim 11 wherein the incapacitating agent is selected from the group consisting of synthetic capsaicin, natural capsaicin, dibenzoxazepine (CR), chloroacetophenone (CN), ortho-chlorobenzalmalononitrile (CS), oleoresin capscium (OC), oleoresin paprika, paprika, capsicums (chili peppers), trans-8-methyl-N-vanillyl-6-nonenamide (capsaicin), 8-methyl-N-vanillyl-nonamide (dihydrocapsaicin), 7-methyl-N-vanillyl-octamide (nordihydrocapsaicin), 9-methyl-N-vanillyl-decamide (homodihydrocapsaicin), trams-9methyl-N-vanillyl-7-decenamide (homocapsaicin), (3R, 3p, 5pR)-3,3'-dihydroxy-a', k-caroten-6'-one (capsanthin), N-vanillyl-octamide, N-vanillyl-nonamide, N-vanillyl-decanamide, N-vanillyl-undecanamide, N-vanillyl-paaiperic acid amide, and mixtures thereof.

13. The method of claim 1 wherein the incapacitating agent is present in an amount of about 0.18% to about 3% by weight of the solvent system.

14. The method of claim 13 wherein the incapacitating agent is present in an amount of about 1.4% to about 1.5% by weight of the solvent system.

15. The method of claim 1 wherein said incapacitating agent comprises an inflammatory agent, and wherein the non-lethal temporarily incapacitating formulation is formulated to cause, upon application of the system to the facial area of a recipient, inflammation to the facial area of the recipient.

16. The method of claim 1, wherein said applying of the non-lethal temporarily incapacitating formulation into the facial area of the subject causes the subject to experience a symptom selected from the group consisting of immediate closing of the eyes, shortness of breadth, and burning sensation.

17. The method of claim 16, wherein the symptom lasted no longer than one hour.

18. The method of claim 1, wherein said applying of the non-lethal temporarily incapacitating formulation into the facial area of the subject causes the subject to experience symptoms comprising immediate closing of the eyes, shortness of breadth, and burning sensation.

19. The method of claim 18, wherein the symptoms lasted no longer than one hour.

20. The method of claim 1, wherein said applying comprises defending oneself by applying the non-lethal temporarily incapacitating formulation into the facial area of the subject.

21. The method of claim 1, wherein said applying comprising applying the non-lethal temporarily incapacitating formulation into the facial area of a person engaged in a bar fight, a domestic disturbance, a hostage situation, a terrorist situation, a barricade situation, or a riot, or a suspect engaged in flight.

22. The method of claim 1, wherein said applying comprises a law enforcement official applying the non-lethal temporarily incapacitating formulation into the facial area of the subject.

23. The method of claim 1 wherein the incapacitating agent is present in an amount of 0.9% or greater by weight of the solvent system.

* * * * *